(12) United States Patent
Noyes (10) Patent No.: US 8,257,723 B2
(45) Date of Patent: Sep. 4, 2012

(54) FILLERS AND METHODS FOR DISPLACING TISSUES TO IMPROVE RADIOLOGICAL OUTCOMES

(75) Inventor: William R. Noyes, Grand Forks, ND (US)

(73) Assignee: Incept LLC, Lexington, MA (US)

( * ) Notice: Subject to any disclaimer, the term of this patent is extended or adjusted under 35 U.S.C. 154(b) by 328 days.

(21) Appl. No.: 12/651,502

(22) Filed: Jan. 4, 2010

(65) Prior Publication Data

US 2010/0160711 A1 Jun. 24, 2010

Related U.S. Application Data

(63) Continuation of application No. 10/602,526, filed on Jun. 24, 2003, now Pat. No. 7,744,913.

(60) Provisional application No. 60/427,662, filed on Nov. 19, 2002, provisional application No. 60/391,027, filed on Jun. 24, 2002, provisional application No. 60/444,143, filed on Jan. 31, 2003.

(51) Int. Cl.
*A61F 13/00* (2006.01)
*A61F 2/00* (2006.01)

(52) U.S. Cl. ......................... 424/422; 424/423; 424/434

(58) Field of Classification Search ........................ None
See application file for complete search history.

(56) References Cited

U.S. PATENT DOCUMENTS

| | | | |
|---|---|---|---|
| 4,193,813 A | 3/1980 | Chvapil | |
| 4,703,108 A | 10/1987 | Silver et al. | |
| 4,970,298 A | 11/1990 | Silver et al. | |
| 5,499,994 A | 3/1996 | Tihon et al. | |
| 5,599,552 A | 2/1997 | Dunn et al. | |
| 5,618,563 A | 4/1997 | Berde et al. | |
| 5,629,008 A | 5/1997 | Lee | |
| 5,681,873 A * | 10/1997 | Norton et al. | 523/115 |
| 5,759,583 A | 6/1998 | Iwamoto et al. | |
| 5,863,984 A | 1/1999 | Doillon et al. | |
| 5,874,500 A | 2/1999 | Rhee et al. | |
| 5,885,829 A * | 3/1999 | Mooney et al. | 435/325 |
| 5,932,539 A | 8/1999 | Stupp et al. | |
| 6,031,148 A | 2/2000 | Hayes et al. | |
| 6,110,484 A | 8/2000 | Sierra | |
| 6,129,761 A | 10/2000 | Hubbell | |
| 6,206,930 B1 | 3/2001 | Burg et al. | |
| 6,224,893 B1 | 5/2001 | Langer et al. | |
| 6,268,405 B1 | 7/2001 | Yao et al. | |
| 6,271,278 B1 | 8/2001 | Park et al. | |
| 6,280,772 B1 | 8/2001 | Pinkus | |
| 6,388,047 B1 | 5/2002 | Won et al. | |
| 6,413,742 B1 | 7/2002 | Olsen et al. | |
| 6,509,031 B1 | 1/2003 | Miller et al. | |
| 6,545,097 B2 | 4/2003 | Pinchuk et al. | |
| 6,761,908 B1 | 7/2004 | Roreger | |
| 6,913,744 B2 | 7/2005 | Gokcen | |
| 2003/0149437 A1 * | 8/2003 | Livne et al. | 606/76 |

FOREIGN PATENT DOCUMENTS

| | | |
|---|---|---|
| CA | 2 188 464 C | 11/1995 |
| DE | 44 14 755 A1 | 1/1996 |
| WO | 99/59501 A1 | 11/1999 |

OTHER PUBLICATIONS

European Office Action dated Jan. 27, 2011 (EP 03 761 283.5-1219)—7 pages.

* cited by examiner

*Primary Examiner* — Robert A Wax
*Assistant Examiner* — Randeep Singh
(74) *Attorney, Agent, or Firm* — Dardi & Herbert, PLLC; Curtis B. Herbert (57) ABSTRACT

Certain embodiments include a method of improvising radiological outcomes by introducing a filler to between a first tissue location and a second tissue location to increase a distance between the first tissue location and the second tissue location, and administering a dose of radioactivity to at least the first tissue location or the second tissue location. Collagen and hyaluronic acid are examples of fillers. Certain embodiments include a medical device having a biocompatible, biodegradable filler material, wherein the device comprises at least a portion that has a shape that substantially conforms to Denovillier's space between the rectum and prostate. Certain embodiments include a kit, the kit comprising a filler and instructions for placing the filler between a first tissue location and a second tissue location to increase a distance between the first tissue location and the second tissue location.

24 Claims, 4 Drawing Sheets

FILLERS AND METHODS FOR DISPLACING TISSUES TO IMPROVE RADIOLOGICAL OUTCOMES

RELATED APPLICATIONS

This application is a Continuation of application Ser. No. 10/602,526, filed Jun. 24, 2003, now U.S. Pat. No. 7,744,913, which claims priority to U.S. provisional patents 60/427,662 filed Nov. 19, 2002, 60/391,027 filed Jun. 24, 2002, and 60/444,143, filed Jan. 31, 2003, which are hereby incorporated herein by reference.

BACKGROUND

Over 198,100 men will be diagnosed with prostate cancer each year. Typically, forty percent will choose interstitial implant therapy, one-third of the men will choose surgery, and one third will choose external beam radiotherapy.

Typical treatments for prostate cancer include surgical removal of the prostate (prostatectomy), freezing the prostate (cryosurgery), hormonal therapy, prostate seed implant therapy, or prostate conformal radiation.

The treatment providing the best outcome is still debatable. However, the side effects of treating prostate cancer have become less toxic and less profound with implant therapy and 3D conformal radiotherapy. Advancements in treatment positioning and target localization have significantly improved outcomes and diminished the side effects.

Since the conception of 3D conformal radiotherapy, physicians have paid attention to the delivered dose to the target and surrounding tissues. Investigators have been able to correlate side effects to the amount of tissue receiving a certain radiation dose. This term has been coined: dose volume histogram. For conformal radiotherapy it is conventionally preferred that the rectum receive less than 40% of the prescribed treatment dose in hopes of minimizing the radiation induced side effects.

Time, distance, and shielding affect the dose that is delivered. The less time an area is exposed to radiation, the less dose delivered. The greater the distance from the radiation, the less dose delivered. Finally, more shielding will also decrease the delivered dose.

SUMMARY OF CERTAIN EMBODIMENTS OF THE INVENTION

It would be desirable to provide a protocol to decrease the radiation dose to the rectum during radiotherapy for prostate cancer. It is also desirable to decrease radiation treatment-induced side effects on sensitive organs resulting from other therapies and applications directed to a target organ. Certain embodiments of the present invention address these issues.

Certain embodiments are a medical device, the device having a biocompatible, biodegradable filler material, wherein the device comprises at least a portion that has a shape that substantially conforms to the space between two tissue locations, e.g., Denovillier's space.

Certain embodiments are a method comprising introducing a filler to between a first tissue location and a second tissue location to increase a distance between the first tissue location and the second tissue location. Further, there maybe a step of administering a dose of radioactivity to at least the first tissue location or the second tissue location.

Certain embodiments are directed to kits having a filler, instructions for placing the filler between tissues in conjunction with a treatment, e.g., radiation or cryogenics, and an optional delivery device.

Certain embodiments may have a filler material that comprises an extracellular matrix molecule. Certain embodiments may have a filler material that is biodegradable in vivo in less than approximately 90 days. Certain embodiments may have at least one therapeutic agent. Certain embodiments may have a buffering agent. Certain embodiments may have a total volume or a volume of filler in the range of about 10 to about 50 cubic centimeters, wither before or after the device or filler is introduced into the patient. An expandable device may be used for filler, e.g., a balloon or sponge. Or the filler material may comprise a synthetic polymer.

DETAILED DESCRIPTION

Certain embodiments of the invention comprise placing a filler between the radiation target tissue and other tissues. The filler increases the distance between the target tissue and other tissues so that the other tissues receive less radiation. In some embodiments, the filler is a degradable material that is installed once prior to the course of radiation treatment and does not require subsequent manipulation, repositioning, or removal. Some fillers maintain their natural properties during and after exposure to radiation and remain in the same location until after a treatment course has concluded. Other embodiments include fillers made with inflatable devices that are introduced between the target tissue and other tissue; such inflatable devices may be left in the patient during the course of radiation treatment or removed and reintroduced periodically during the course of radiation treatment. Certain of the embodiments set forth herein address various advantages that are described in the context of the evolution of the prostate treatment procedures.

The modern era has witnessed the evolution of radical prostatectomy, external beam radiotherapy and interstitial permanent seed Brachytherapy to a point where the results are nearly equivalent. Although some authors may debate that their technique has achieved superior results, by and large the results have been too close to claim that one modality is definitely superior to the other. If this is so, then the decision for therapy must consider treatment related side effects.

External beam radiotherapy may cause radiation-induced side effects for prostate cancer. Modern radiation treatment using 3D conformal therapy and most recently, intensity modulated radiotherapy (IMRT) has significantly reduced treatment related side effects. However, such treatments continue to require special consideration for the rectum, which is particularly sensitive to radiation. Care is taken to ensure that the rectum receives a dose that is well tolerated and diminishes the probability of treatment related side effects. Others have evaluated the effectiveness of daily insertion of rectal catheters and daily administration of rectal radioprotectants, and have achieved only modest success.

Some investigators are attempting to decrease the dose to the anterior rectal wall and thereby decrease the potential for radiation induced side effects on the rectum. One such technique is to insert an inflatable Foley catheter into the rectum on a daily basis during radiation treatments. The premise is that more of the rectum is displaced away from the prostate than the small portion of rectum that is pushed toward the prostate. Therefore a smaller amount of rectum is receiving radiation and consequently the side effects from radiation should be diminished.

However, certain embodiments set forth herein have advantages that may include the reduction of radiation side effects, improved cost effectiveness, the need to perform only one or a few procedures to achieve a reduction in radiation, no requirement for removal of the treatment after its administration, and ease of use, e.g., by a patient, nurse, or technician.

Example 2 includes a study that shows that injection of human collagen into Denovillier's space can change the radiation dose that the rectum receives when the prostate is exposed to radiation. "Denovillier's space" is a region located between the rectum and prostate. The collagen was well tolerated and withstood the radiation treatments. The collagen degraded in less than about sixty days and required no procedures after its initial introduction into the patients. The study was a trial involving 10 men who received human collagen injections into Denovillier's space to displace the rectum away from the prostate prior to proceeding with their radiotherapy. The injections were well tolerated and could readily be performed on an outpatient basis. The radiation dose to the rectum was diminished by over approximately 50% when 20 cc's of human collagen was injected into Denovillier's space. Moreover, men who have received human collagen injections appeared to have minimal rectal side effects associated from their radiotherapy and had no appreciable changes associated due to the collagen.

This procedure was well-tolerated by the patients. Indeed, others have reported that human collagen has been used in various body areas and is well tolerated. For example, it has been injected into a the perineum in hopes of improving urinary incontinence. And human collagen has received United States Food and Drug Administration approval to be used in brachytherapy procedures as a spacer. Further, it is known that normal saline may be injected into the potential space between the rectum and prostate prior to proceeding with cryotherapy to minimize the freezing effect on the rectum, so displacement of the tissues around Denovillier's space is known to be well-tolerated.

The successful use of collagen as a filler shows that other materials may also be used. Other materials may include natural or synthetic materials, e.g., proteins, extracellular matrix molecules, fibrin, proteins, hyaluronic acid, albumin, bulking agents, and polyethylene glycol-based materials. A synthetic material is a material that is not found in nature.

Certain embodiments provide a method of displacing a tissue to protect the tissue against the effects of a treatment involving radiation or cryotherapy. One embodiment involves using a filler to displace the tissue relative to a tissue that is to receive the treatment. Another embodiment involves introducing a filler to displace a first tissue and radiating a second tissue, particularly a second tissue that is close to the first tissue. In another embodiment, the method comprises the steps of injecting a filler into a space between tissues; and may further include irradiating one of the tissues so that the other tissue receives less radiation than it would have in the absence of the filler.

Certain embodiments also provide methods for treating a tissue of a body by radiation. In one embodiment, the method comprises the steps of injecting an effective amount of a filler into a space between a first tissue (e.g., prostate) of a body and a second tissue (e.g., rectum), which can be a critically sensitive organ; and treating the first tissue by radiation whereby the filler within the space reduces passage of radiation into the second tissue. Tissue is a broad term that encompasses a portion of a body: for example, a group of cells, a group of cells and interstitial matter, an organ, a portion of an organ, or an anatomical portion of a body, e.g., a rectum, ovary, prostate, nerve, cartilage, bone, brain, or portion thereof.

Also provided are embodiments for displacing a sensitive body tissue relative to another body tissue that is the target of a treatment protocol, to effectively reduce side effects on/in the sensitive tissue induced by or resulting from a treatment directed to the target tissue. In one embodiment, the method comprises injecting a filler into a space between the sensitive body tissue (e.g., rectum) and the target body tissue (e.g., prostate); and conducting a treatment protocol on the target body tissue whereby the sensitive body tissue is less affected by the treatment as a result of the presence of the filler.

Examples of embodiments of the treatment include use with such applications as external beam radiotherapy (e.g., 3D conformal or Intensity Modulated Radiotherapy), interstitial prostate brachytherapy (e.g., using permanent or temporary seeds, or using High Dose Rate remote after loading), and cryosurgery. Another embodiment is the use of these techniques for brachytherapy radiation treatments for prostate cancer or gynecological cancers. Brachytherapy includes the placement of a radioactive isotope within or near the tumor, target organ, or other tissue. For example, a brachytherapy technique is placement of permanent I-125 radioactive seeds into the prostate for treatment of prostate cancer. Applications for gynecology include embodiments involving displacing a tissue from another tissue that is to be targeted by radiation.

A filler is a substance that occupies a volume after its introduction into a body. Examples of fillers include but are not limited to polymers, gels, sols, hydrogels, sponges, bulking agents, and balloons. Filler materials include polysaccharides, alginate, collagen, gelatin, fibrin, fibrinogen, albumin, serum, autologous serum, sutures, and natural and synthetic polymers. Synthetic polymers include polylactide, polyglycolide, polycaprolactones, poly(alpha.-hydroxy acid), poly (amino acid), and poly(anhydride). Fillers may be crosslinked or uncrosslinked. Polymers include polyethylene glycol and derivatives thereof, including crosslinked polyethylene glycols. Other types of polymers include thermoreversible and thixotropic polymers. Other examples of a filler include self-absorbing suture material held within a suspension (such as prolene sutures).

Fillers may include materials that are formed in situ in the body, e.g., by combining a first precursor and a second precursor to form a material, e.g., a gel or hydrogel. Examples include covalent bonding of electrophiles and nucleophiles (e.g., see U.S. Pat. No. 5,874,500) and gelation of polysaccharides (e.g., addition of calcium to alginate). Fillers may include materials derived from the body that receives them, e.g., autologous serum. Donor blood may be used to derive some materials, e.g., albumin. Combinations of materials are also contemplated.

Suitable fillers and materials for fillers may include, for example, those set forth in U.S. Pat. Nos. 6,509,031; 6,413, 742; 6,388,047; 6,280,772; 6,271,278; 6,268,405; 6,129,761; 6,031,148; 6,110,484; 5,932,539; 5,874,500; 5,863,984; 5,865,367; 5,759,583; 5,618,563; 5,599,552; 4,970,298; 4,703,108; and 4,193,813, which are hereby incorporated by reference in their entirety herein.

Fillers may be biodegradable, either by hydrolysis, proteolysis, the action of cells in the body, or a combination thereof. Biodegradation may be measured by palpitation or other observations to detect the change in volume of a filler after its introduction into a patient. Biocompatible materials are preferred, especially collagen or hyaluronic acid. A suitable length for biodegradation to occur is between one day and twelve months after introduction of the filler into the body. Alternatively, fillers may remain in place for other periods, including from one week to three months and two to eight weeks. Also the filler may be biodegraded in less than about two months after implantation, as is preferable for the case of displacing rectal tissue from the prostate gland. The time for biodegradability for a specific use may be determined by the time required to complete a course of radiation, which may vary for different radiological applications and different requirements for administering the full course of radiological therapy.

Fillers may include osmotic agents. For example, agents that increase the osmotic pressure of the filler may be used in the filler. One advantage of an osmotic agent is that it will cause the filler to increase its volume after its introduction into the body. For example, albumin, human serum, human plasma, salts, or steroids may be added to, or mixed with, the filler.

Fillers may contain drugs or be used to deliver drugs. For example, a steroid may be introduced into the filler. Drugs may include, for example, steroids, anti-inflammatory agents, agents to inhibit degradation of the filler (e.g., protease inhibitors), agents to enhance filler degradation, antibiotics, hemostatics, and antimycotics.

Fillers may also be reversibly introduced. For example, a thermoreversible polymer may be introduced as a liquid-like material and allowed to form a gel in situ. Or a polymer may be introduced that is non degradable or poorly degradable until it is heated to cause its degradation or liquefaction.

A filler may have a first physical state before its introduction into the body and a second physical state after its introduction into the body. A change in physical state may include, for example, a change in volume, viscosity, water content, swelling, or crosslinking. Another embodiment is a filler that exists as at least two precursors before introduction into the body and exists as a crosslinked material formed by the mixing of the two precursors after introduction into the body.

For example, solutions containing collagen or collagen-like precursors may be introduced into the body. As the solution warms to the body temperature as the pH of the solution becomes adjusted to bodily pH, the fibrils cooperate to form a fibrin gel according to well-known processed of collagen formation. The solution has a low viscosity while stored, e.g., as part of a kit, but has a stronger physical structure after its self-assembly in situ in the patient.

And for example, solutions of polysaccharides may be introduced into the patient. Some polysaccharides increase in viscosity when exposed to certain salts, or in response to a change in pH. Products and processes involving, for instance, hyaluronic acid solutions or precursors that gel after introduction into a patient are known.

Thermoplastic polymers include pharmaceutically compatible polymers that are bioerodible by cellular action, are biodegradable by action of non-living body fluid components, soften when exposed to heat but return to the original state when cooled and are capable of substantially dissolving or dispersing in a water-miscible carrier or solvent to form a solution or dispersion. Upon contact with an aqueous fluid and the dissipation of the solvent component the thermoplastic polymers are capable of coagulating or solidifying to form a solid or gelatinous matrix suitable for use as an implant in an animal. The kinds of thermoplastic polymers suitable for the present composition generally include any having the foregoing characteristics. Examples are polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or combinations or mixtures therein. Polylactides, polycaprolactones, polyglycolides and copolymers thereof are highly preferred thermoplastic polymers.

The thermoplastic polymer is combined with a suitable organic solvent to form a solution. The solubility or miscibility of a polymer in a particular solvent will vary according to factors such as crystallinity, hydrophilicity, capacity for hydrogen-bonding and molecular weight of the polymer. Consequently, the molecular weight and the concentration of the polymer in the solvent are adjusted to achieve desired miscibility. Highly preferred thermoplastic polymers are those which have a low degree of crystallization, a low degree of hydrogen-bonding, low solubility in water, and high solubility in organic solvents.

The composition of the invention may as well be a liquid formulation of a thermosetting oligomeric pre-polymer or copolymer which is capable of cross-linking or hardening to provide a microporous gelatinous or solid matrix suitable for use as an implant in an animal, including a human. The thermosetting pre-polymers and resulting cross-linked polymers and copolymers are biocompatible, and biodegradable and/or bioerodible.

The pre-polymers are preferably low molecular weight polymers or oligomers having end functional groups that are reactive with acryloyl chloride to produce acrylic ester-terminated pre-polymers. Acrylic pre-polymers for use in the compositions may be synthesized according to a variety of methods including, but not limited to, reaction of a carboxylic acid, such as acrylic or methacrylic acid, with an alcohol; reaction of a carboxylic acid ester, such as methyl acrylate or methyl methacrylate, with an alcohol by transesterification; and reaction of an isocyanatoalkyl acrylate, such as isocyanatoethyl methacrylate, with an alcohol.

The thermosetting prepolymers are also short chain polyol derivatives of the thermoplastic polymers described herein. The polyol terminated derivatives are converted to acrylic ester terminated prepolymers by any suitable method. Examples are short chain polyol derivatives of polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or combinations or mixtures therein.

A polymer matrix and implant prepared with thermosetting prepolymers is composed of poly(DL-lactide-co-caprolactone) (DL-PLC). To prepare the DL-PLC polymer matrix, DL-lactide or L-lactide and .gamma.-caprolactone are co-polymerized in the presence of a multifunctional polyol initiator and a curing agent to produce hydroxy-terminated PLC prepolymers. This polyol-terminated pre-polymer is then converted to an acrylic ester-terminated pre-polymer by any suitable method, as for example, by acylation of the alcohol terminus with acryloyl chloride by means of, for example, a Schotten-Baumann technique (reaction of acyl halide with alcohol).

Optionally, a curing agent, such as a catalyst, may be added to the acrylic pre-polymer mixture to enhance cross-linking of the prepolymers and the subsequent coagulation or solidification of the resulting polymer to form a matrix. For example, the acrylic pre-polymer, in an amount of about 5 grams, may be added to a solution of benzoyl peroxide (BP) in about 1 ml of $CH_9Cl_2$. Optionally, other acrylic monomers may be added to the acrylic pre-polymer mixture before adding the curing agent. The acrylic pre-polymer mixture may be cured in air at room temperature, or in a preheated vacuum oven.

Preferred catalysts for the preparation of the PLC prepolymers are basic or neutral ester-interchange (transesterification) catalysts, as for example, metallic esters of carboxylic acids containing up to 18 carbon atoms, formic, acetic, lauric, stearic, and benzoic acid. Preferred catalysts include, for example, stannous octoate and stannous chloride.

A multi-functional polyol chain initiator may be included in the thermosetting polymer compositions to vary the molecular weight and composition of the polymer. For example, a bifunctional chain initiator such as ethylene glycol, may be included to produce a bifunctional polymer, or a trifunctional initiator, such as trimethylolpropane, may be used to produce a trifunctional polymer. Further, the molecular weight of the polymer or co-polymer may be varied according to the concentration of the chain initiator in the composition. For example, a high concentration of a bifunctional chain initiator may make available an initiator molecule for each polymer chain, while a low concentration may contain one initiator molecule for every two polymer chains.

Following the addition of the curing agent, the pre-polymer polymer mixture preferably remains in liquid form for a period of time effective to allow administration of the composition to the implant site. Thereafter, the cross-linking reaction preferably continues until a solid or gelatinous polymer matrix is produced. Accordingly, the pre-polymer mixture cures, or solidifies, in situ to form a polymer matrix which is capable of biodegradation and/or bioabsorption over time.

A solution that contains a filler gels in response to a change in pH may be made up at a first pH in solution, but be buffered so that its pH changes after introduction into a patient. The buffer could be relatively weak compared to physiological buffer saline solutions, or it could be concentrated. In either case, the buffer would eventually diffuse away so that the pH of the filler would be changed.

Similarly, a solution having a filler that changes viscosity, crosslinks, or gels in response to a change in temperature could be introduced at a first temperature and allowed to transition to body temperature in situ in a patient so that it would have a change in properties.

Fillers may be mixed with salts, buffers, or other pharmaceutically acceptable agents, e.g., carriers. Examples of suitable pharmaceutical carriers are described, for example, in "Remington's Pharmaceutical Sciences" by E. W. Martin. Examples of buffers include phosphates, carbonates, and Tris. Examples of buffer osmolarity are ranges from 10 to 3000, from 50 to 600, from 150 to 500, and from 300-350. A buffering agent may be both a buffer and an osmolarity agent. Fillers may also be mixed with agents to aid their visualization by medical devices, e.g., by MRI or ultrasound. Fillers may also be mixed with agents that block radiation.

If the filler contains collagen, the collagen may be natural or synthetic collagen, and of human origin or non-human origin, such as bovine collagen (e.g., Bovine Type I collagen), for example. The collagen can be prepared as a suspension with a pharmaceutically acceptable vehicle or carrier (e.g., water) having a pH in the physiological range. Collagen may be collagen derived from a natural source, and may includes collagen isolated from tissue and recombinantly derived collagen, e.g., collagen produced by genetically engineered bacteria. Collagen may also be collagen that is not found in nature, e.g., materials intelligently designed to mimic collagen or some of the structural or functional features of collagen.

Polymeric materials which are capable of forming a hydrogel may be utilized. In one embodiment, the polymer forms a hydrogel within the body upon contact with a crosslinking agent. A hydrogel is defined as a substance formed when an organic polymer (natural or synthetic) is crosslinked via covalent, ionic, or hydrogen bonds to create a three-dimensional open-lattice structure which entraps water molecules to form a gel. Naturally occurring and synthetic hydrogel forming polymers, polymer mixtures and copolymers may be utilized as hydrogel precursors.

Examples of materials which can be used to form a hydrogel include modified alginates. Alginate is a carbohydrate polymer isolated from seaweed, which can be crosslinked to form a hydrogel by exposure to a divalent cation such as calcium, as described, for example in WO 94/25080. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemical modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or .epsilon.-caprolactone. The resulting polymer includes alginate blocks which permit ionically catalyzed gelling, and oligoester blocks which produce more rapid degradation depending on the synthetic design. Alternatively, alginate polymers may be used, wherein the ratio of mannuronic acid to guluronic acid does not produce a firm gel, which are derivatized with hydrophobic, water-labile chains, e.g., oligomers of .epsilon.-caprolactone. The hydrophobic interactions induce gelation, until they degrade in the body.

Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives are particularly useful. As used herein, the term "modified hyaluronic acids" refers to chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme, Cambridge, Mass. and Fidia, Italy.

Other polymeric hydrogel precursors include polyethylene oxide-polypropylene glycol block copolymers such as PLURONICS or TETRONICS, which are crosslinked by hydrogen bonding and/or by a temperature change, as described in Steinleitner et al., Obstetrics & Gynecology, 77:48-52 (1991); and Steinleitner et al., Fertility and Sterility, 57:305-308 (1992).

Other materials which may be utilized include proteins such as fibrin, collagen and gelatin. Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethyleneglycol, polyoxyethylene) 100,000 can be combined to form a gel over the course of time, e.g., as quickly as within a few seconds.

Covalently crosslinkable hydrogel precursors also are useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669. In this embodiment, water soluble macromers that include at least one water soluble region, a biodegradable region, and at least two free radical-polymerizable regions, are provided. The macromers are polymerized by exposure of the polymerizable regions to free radicals generated, for example, by photosensitive chemicals and or light. Examples of these macromers are PEG-oligolactyl-acrylates, wherein the acrylate groups are polymerized using radical initiating systems, such as an eosin dye, or by brief exposure to ultraviolet or visible light. Additionally, water soluble polymers which include cinnamoyl groups which may be photochemically crosslinked ma be utilized as disclosed in Matsuda et al., ASAID Trans., 38:154-157 (1992).

Water soluble polymers with charged side groups may be crosslinked by reacting the polymer with an aqueous solution containing ions of the opposite charge, either cations if the polymer has acidic side groups or anions if the polymer has basic side groups. Examples of cations for crosslinking of the polymers with acidic side groups to form a hydrogel are monovalent cations such as sodium, and multivalent cations such as copper, calcium, aluminum, magnesium, strontium, barium, and tin, and di-, tri- or tetra-functional organic cations such as alkylammonium salts. Aqueous solutions of the salts of these cations are added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

Other examples of fillers are hyaluronic acid, cellulose, alginate, and gelatin, which are available from commercial sources, e.g., Sigma-Aldrich, Inc. and ICN Biomedicals, Inc. Hyaluronic acid is a material that is accepted in the medical community as a material that may be implanted into a patient; other commercial sources are Genzyme Advanced Biomaterials (e.g., HyluMed®), LifeCore Biomedical, and FMC BioPolymer. Another example of a filler is cellulose, e.g., Avicel® a thixotropic cellulose product from FMC BioPolymer. Another filler example is synthetic polymer hydrogels, e.g., as made by Angiotech Pharmaceuticals, e.g., Coseal®. Other fillers are described in, e.g., U.S. Pat. No. 6,224,893, and other references set forth herein.

Another embodiment is a filler that comprises a device having a reversible volume, for example, a balloon. A balloon may be introduced, inflated, and then deflated after a dose of radiation has been administered, or recovered after the radiation treatment has been completed.

In use, a device for delivering a filler to a body may be loaded with a filler, and the filler introduced into the body, preferably so that the distance between a first and a second tissue in the body is thereby increased. A further step may include administering a dose of radiation to a tissue, preferably so that the second tissue receives less radiation than it would have received if the distance between the first and second tissue had not been increased. A further step may also be administration of cryogenic treatment to the first or second tissue or a tissue nearby. The radiation may alternatively be directed to a third tissue so that the first tissue or the second tissue received a lower amount of radiation as a result of its separation from the other tissue(s). The first tissue and the second tissue may be adjacent to each other in the body, or may be separate from each other by other tissues. In many cases, such separation does not reduce the beneficial effects of achieving separation between the first and second tissue.

Filler volumes for separating tissues are dependent on the configuration of the tissues to be treated and the tissues to be separated from each other. In many cases, a volume of about 20 cubic centimeters (cc's or mls) is suitable. In other embodiments, as little as 1 cc might be needed. Other volumes are in the range of 5-1000 cc, and all ranges therebetween, e.g., 5-400 cc, 10-30 cc, 15-25, cc, 10-150 cc, 20-200 cc, 15-500 cc, 50-1000 cc, and 30-200 cc. In some embodiments, filers are administered in two doses at different times so as to allow the tissues to stretch and accommodate the filler and thereby receive a larger volumes of filler than would otherwise be readily possible.

An example of a delivery device is a syringe. The filler is loaded into the syringe and injected through a needle into a body. Another example is a device that accepts, e.g., a folded, deswelled, or rolled filler and provides a propelling mechanism to propel the filler through a needle or catheter into a body. Propulsion may be by, e.g., a handle, a plunger, gas, or liquid force.

Another embodiment is a kit for introducing a filler into a body. The kit may include a filler and a device for delivering the filler to the body. The filler may be capable of undergoing a change in state after its introduction into the body: for example, a collagen solution forms a collagen gel after entering the body, and a dehydrated sponge imbibes water to increase its volume after exposure to physiological conditions. Embodiments include instructions for use. Embodiments include anesthetics mixed with the filler or separate therefrom. Embodiments include kits wherein the delivery device is a syringe, and other embodiments include a needle for the syringe, and may include a needle for administering the filler and/or the anesthetic.

Instructions may be included with a kit. Instructions may include words that direct a user in a use of a kit. Instructions may be fully or partially included with the kit, including as an insert, on a label, on a package, in a brochure, a seminar handout, a seminar display, an internet teaching course, or on an internet or intranet web site. For example, a label on a kit could reference an internet address having instructions. Instructions may include explanations of embodiments set forth herein. Instructions may include dose histograms, and explanations of suitable filler volumes for use.

Preferred anesthetics are local anesthetics, particularly 1% lidocaine for use in applying a filler to a body to displace the rectum from the prostate gland. The lidocaine may be used to perform a nerve block. A preferred needle for anesthetic application is a short 22-gauge needle and a 7 cm 22-gauge spinal needle. A preferred needle for delivering a filler via syringe injection is an 8-gauge spinal needle that is 3.5 cm length. Kist may include anesthetics.

EXAMPLE 1

Sample Protocol

This example describes a protocol for reducing the radiation exposure of a tissue by increasing the distance between the tissue and a nearby tissue that is to be target for radioactive treatment. This example is cast in terms of using a space between the rectum and prostate, but any two tissues, or portions thereof, may be separated by following this protocol and introducing the filler between the tissues instead of into Denovillier's space. Human collagen is used as the filler, but other fillers may be substituted.

Protocol:
a) Inject human collagen into the space (Denovillier's space) between the rectum and prostate.
b) Administer an effective volume of human collagen into Denovillier's space to decrease the radiation dose to the rectum during radiation therapy of the prostate, and change the rectal dose volume histogram.
c) Assess the effectiveness of human collagen in lowering the dose of radiation to the rectum during prostate radiation therapy.
d) Evaluate the acute side effects of radiation during therapy compared to historical controls.

Patient eligibility:
a) Male with biopsy-proven prostate cancer.
b) Age: >18 years of age.
c) Elected conformal radiotherapy for cure or for palliation, i.e., local control due to known metastases.
d) Suitable to undergo a transrectal ultrasound for determination of space between rectum and prostate.
e) Suitable to receive a local anesthetic prior to receiving the human collagen injection.
f) Tolerated a subcutaneous injection of human collagen to rule out hypersensitivity to the collagen products.
g) Signed a study specific consent form.

Patient Contraindications:
a) Allergic to human collagen injection.
b) Does not tolerate human collagen injection for any reason.

Protocol Treatment—Methods and Materials
A. Prior to proceeding with the collagen injection, a diagnostic CT scan of the pelvis or a planning CT scan of the pelvis will be performed with the patient in the supine treatment position. Prior to obtaining the planning CT scan, a Foley catheter will be inserted into the bladder and drained. Fifty cc's of 50% diluted Conray will be instilled into the bladder for visualization. The Foley catheter will then be removed. Five cc's of 50% diluted Conray will be injected into the penile urethra and retained with a penile clamp for delineation. A rectal tube will be inserted into the rectal vault. Thirty-five cc's of diluted contrast will be injected into the rectal vault for delineation. The planning CT scan of the pelvis will be obtained.

The outside surface of the prostate, bladder and rectum will be contoured (e.g., computer outlining of organs). The rectal contour will extend from the anal verge up to the rectosigmoid junction or to the top of seminal vesicles, whichever is greater, provided there is adequate pelvic parenchymal space so that minimal radiation dose is delivered to the upper rectum.

A complex 3-D isodose treatment plan with a 3-D rectal dose volume histogram (DVH) will be generated using a conformal six-field technique. Pre-injection and post-injection measurements will be determined between the anterior rectal wall and the posterior border of the prostate.

B. Procedure to place the filler.
The patient will be placed in the dorsolithotomy position with both legs up in stirrups. The transrectal ultrasound probe will be placed within the rectal vault. A syringe with a 20-gauge needle will be used to administer a local anesthetic. Preferably, a nerve block is performed to the inferior branch of the pudendal nerve using a 7 cm 22-gauge spinal needle to administer 5 cc of 1% lidocaine to the left and right para-vesicular region located just laterally of the seminal vesicles. A second syringe with a 16-gauge spinal needle will be inserted into the perineum and rotated to increase the potential space between the rectum and prostate. The same syringe will inject normal saline into the space between the rectum and prostate to further increase the capacity of this potential space.

Once the normal saline has been injected, a third syringe with a 16-gauge spinal needle will be used to inject a 5-10 mm layer of human collagen along the posterior wall of the prostate between the prostate and rectum. Once the collagen has been injected into the space between the rectum and prostate, ultrasound images will be obtained to determine the echogenicity of the collagen as well as to correlate the measured ultrasound volume to the CT obtained volume. All used syringes will be discarded in a safe manner.

C. A second planning CT scan of the pelvis with simulation will be performed after placement of the collagen injection using the same technique. A 3-D computer generated isodose treatment plan will be generated with a rectal DVH. Differences between the rectal DVH's will be noted.

D. The patient will than proceed with the conformal radiotherapy to a dose of about 7560 cGy in 42 daily treatment fractions.

E. During the course of treatment, the patient will be monitored for changes in bowel frequency, symptoms of proctitis, and amount of medications used if necessary.

F. A third planning CT with simulation will be performed on the first five patients after they have received 15-20 daily radiation treatments. If there has been no significant reduction in collagen volume nor significant changes in the rectal dose per the DVH, the third planning CT scan will be discontinued.

G. A fourth planning CT scan with simulation will be performed on the last day of treatment. Again, a 3-D complex computer plan will be generated to determine the rectal DVH. Measurements will be compared to the previous DVH's. If there has been no significant reduction or change in collagen volume nor significant changes in the rectal dose per the DVH, the fourth planning CT will be discontinued after 20 patients.

H. A fifth planning CT scan with simulation and simulation for dosimetric purposes will be performed approximately 4-6 months after completion of the radiation therapy or 6-8 months after the injection of collagen into the space between the rectum and prostate. This scan will be performed for the first five patients and than discontinued.

Treatment Evaluation:
The results will provide the following information:
Toleration of injection of human collagen into the space between the rectum and prostate.
Extent of anterior displacement of prostate from injection of human collagen.
Amount of radiation dose delivered to anterior wall of rectum.
Amount of dose reduction to rectum per dose volume histogram (DVH).
Clinical changes of bowel habits and treatment intervention during the course of radiation treatments, if any.

Descriptive Factors:
Relationship of cc's of human collagen to forward displacement of prostate.
Description of homogeneous distribution of human collagen between rectum and prostate as determined per ultrasound and CT scan.
Relationship of cc's of human collagen to change of rectal dose volume histogram.

Nursing Evaluation and Treatment Follow-Up:
A weekly assessment of patients will include a review of tolerance of treatment, bowel habit changes and treatment interventions. Typically, medical interventions can include but are not limited to anti-hemorrhoidal creams/ointments, anti-diarrhea medications, anti-spasmodic medications, alpha-1 inhibitors and analgesics with or without narcotics.

Patient review will be conducted at 2 weeks, 1 month, 3 months and 6 months after completion of radiation therapy. The patient will than be followed on a routine serial basis that is recommended for all cancer patients after receiving radiation therapy.

|  | Number of BM's per day | Consistency Normal = N Soft = S Hard = H Loose = 1 | Anal Discomfort | Anti-diarrhea Medication | Anti-Hemorrhoid Medication | Incontinence of Urine (U) or Stool (S) |
|---|---|---|---|---|---|---|
| Consultation |  |  |  |  |  |  |
| Day 1 of XRT |  |  |  |  |  |  |
| Wk 1 |  |  |  |  |  |  |
| Wk 2 |  |  |  |  |  |  |
| Wk 3 |  |  |  |  |  |  |
| Wk 4 |  |  |  |  |  |  |
| Wk 5 |  |  |  |  |  |  |
| Wk 6 |  |  |  |  |  |  |
| Wk 7 |  |  |  |  |  |  |
| Wk 8 |  |  |  |  |  |  |
| 2 Weeks |  |  |  |  |  |  |
| 1 Month |  |  |  |  |  |  |
| 3 Months |  |  |  |  |  |  |
| 6 Months |  |  |  |  |  |  |
| 1 Year |  |  |  |  |  |  |
| 1.5 Years |  |  |  |  |  |  |
| 2 Years |  |  |  |  |  |  |
| 2.5 Years |  |  |  |  |  |  |
| 3 Years |  |  |  |  |  |  |

Human Collagen:

Human collagen is commercially available from multiple manufacturers. Human collagen has been FDA approved to be injected into patients and in particular the pelvis and perineurium of humans. The FDA has also approved the use of human collagen during radiation brachytherapy. Brachytherapy will deliver a dose that is believed to be immeasurable at the surface of the radioactive isotope but can range from 300-600 Gy or greater. The traditional radiation dose delivered to the prostate ranges from 70-76 Gy. However, modern technology using 3-D conformal radiation or Intensity Modulated Radiotherapy (IMRT) has allowed dose escalation upwards to 100 Gy. These doses are well below the dose of 145 Gy used for brachytherapy or the surface dose of a radioactive isotope.

Human collagen is typically commercially supplied in preloaded syringes containing 5 or 10 cc's of collagen. The unit is sterile and comes sealed. The pack will be stored and inspected for damage prior to being opened. If one suspects a damaged product, it will not be used. The human collagen will be removed from its package only prior to undergoing the injection procedure as previously outlined.

Protocol. A syringe with an anesthetic will be used to obtain local anesthesia. A second needle will be inserted into the perineum between the potential space between the rectum and prostate. This needle will be rotated to further open the space between the rectum and prostate (Denovillier's space), and normal saline will then be injected to further increase this potential space. The human collagen will then be injected into this space using ultrasound guidance.

Once the human collagen has been injected into the perineum as desired, the used syringes will be discarded in a safe manner.

EXAMPLE 2

Treatment of Ten Males

This protocol involved injecting an effective volume of human collagen into Denovillier's space to displace the rectum away from prostate. A conventional computer plan used for radiation treatment planning was used to determine the reduction of dose to the rectum (dose volume histogram) corresponding to the collagen injection. Accordingly, patients were monitored during their 2 months of radiation treatments to assess acute radiation induced side effects.

Ten men with stage 1 or stage 2 prostate cancer were informed of the ongoing procedure and elected to participate.

Figure 1:
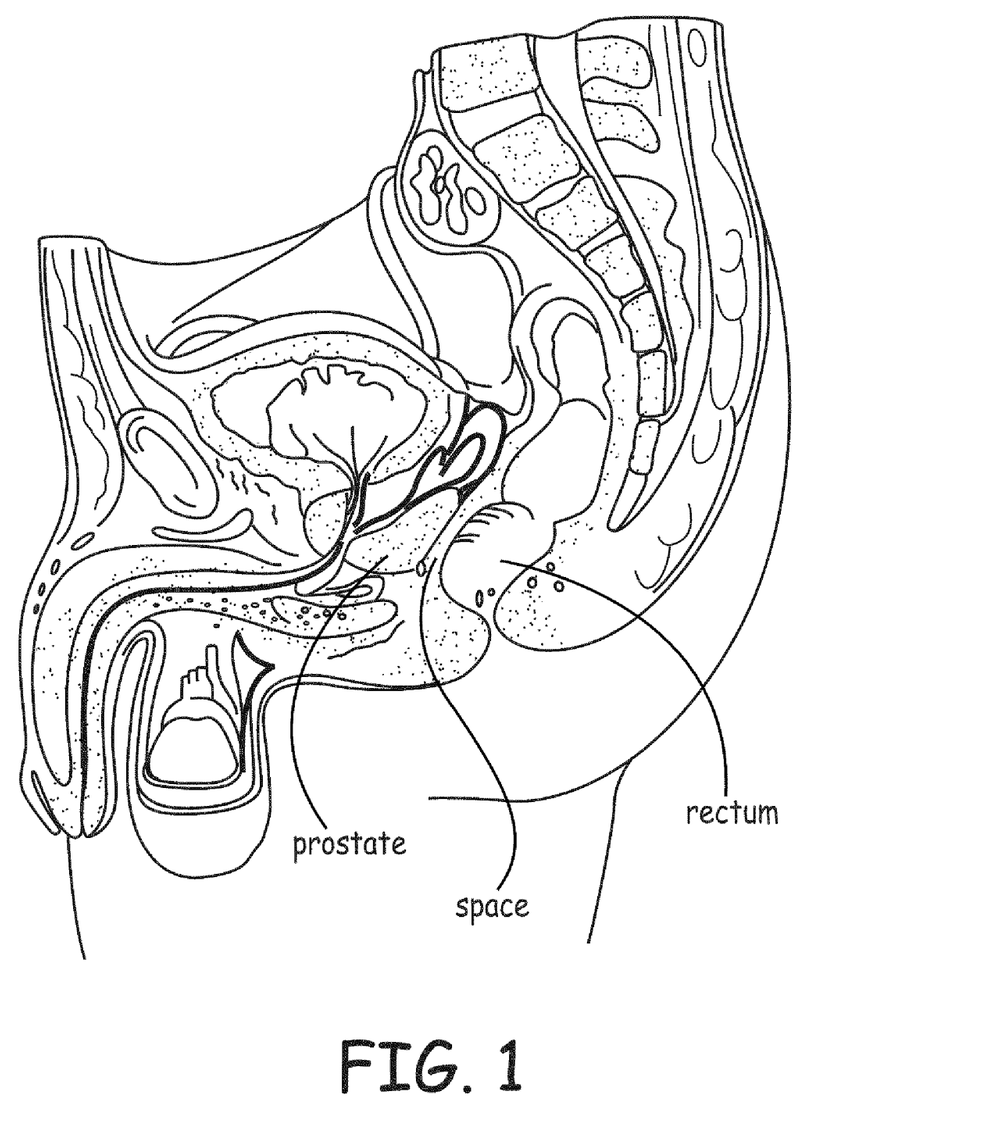
FIG. 1 depicts the male prostate, rectum and Denovillier's space between the prostate and rectum.
Figure 2:
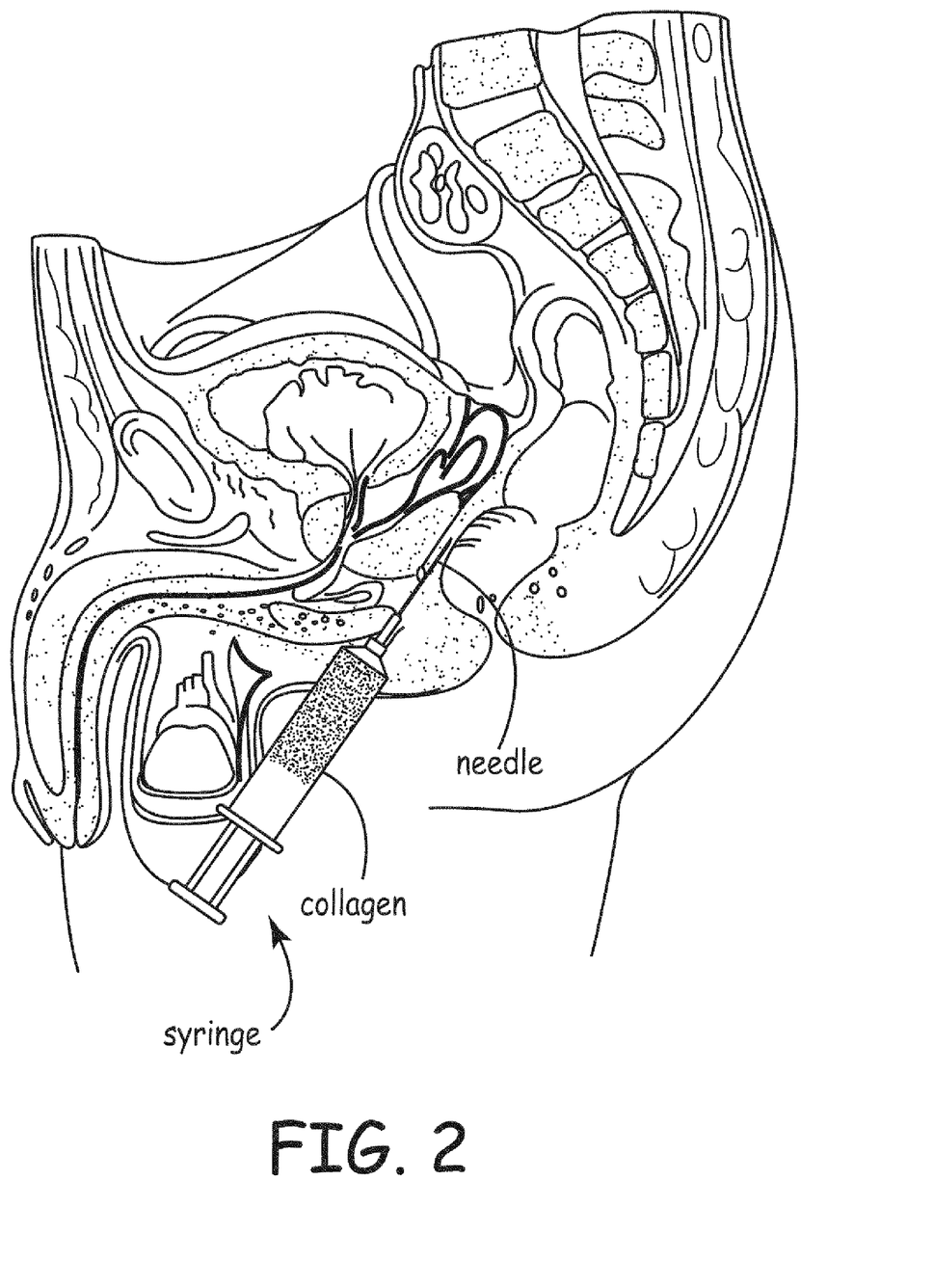
FIG. 2 depicts the insertion of a needle into the space between the prostate and rectum for injecting collagen therein.
Figure 3:
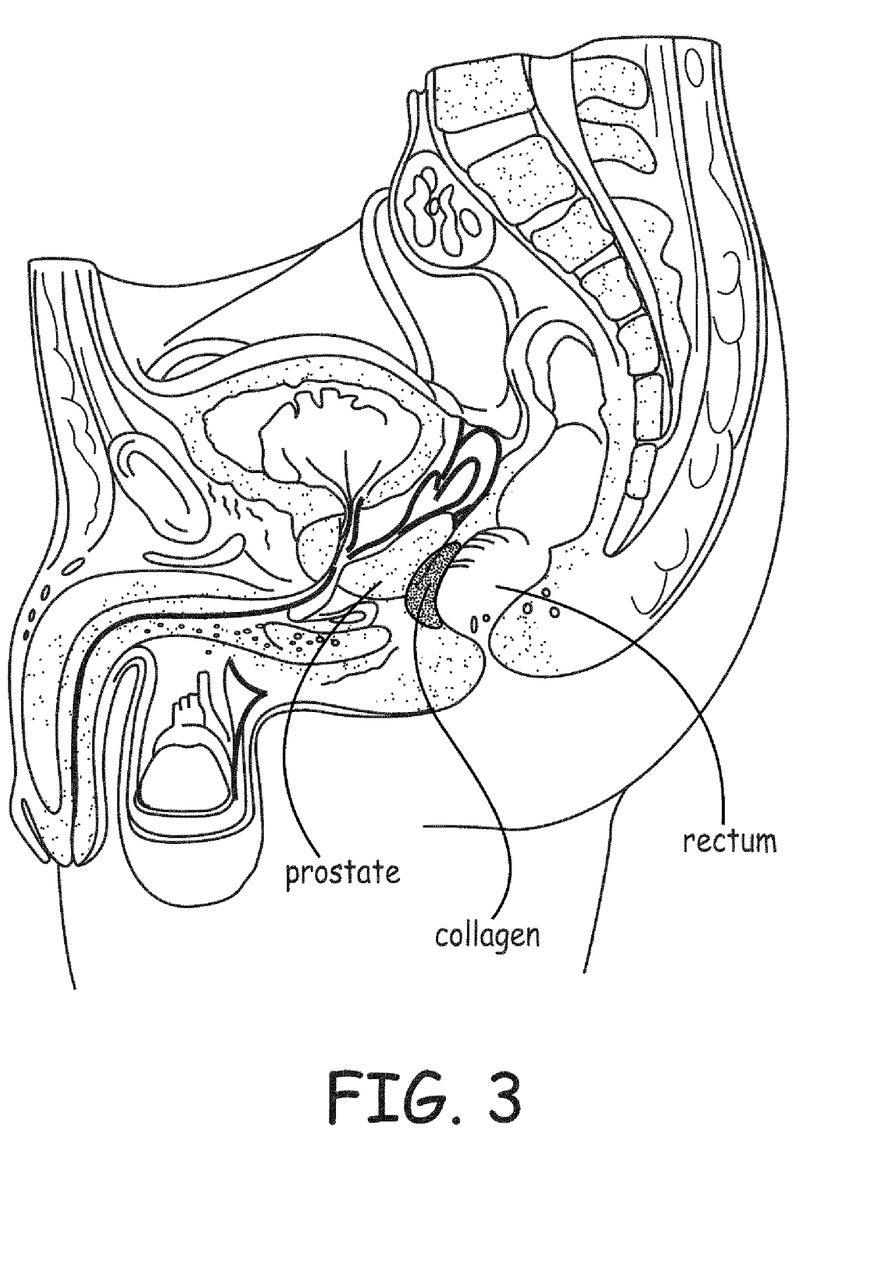
FIG. 3 depicts the injected collagen within Denovillier's space between the prostate and the rectum.

Prior to the collagen injection, each patient underwent a CT simulation to obtain CT images to be used for a radiation computer intensity modulated radiotherapy (IMRT) treatment plan without human collagen. All men received their human collagen injection from the same urologist as an outpatient. To perform the injection, each man was placed in the left lateral decubitis position. An ultrasound transducer was positioned into the rectum so that the entire prostate was well visualized. A 7 inch 22 gauge spinal needle was used to perform a bilateral pudendal nerve block using 2% lidocaine. After obtaining adequate anesthetic effect, a 5.5 inch 18 gauge spinal needle was positioned into the space between the rectum and prostate using ultrasound guidance. Once the needle location was believed to be within Denovillier's space, 5-10 cc's of normal saline was injected to open the potential space between the rectum and prostate. Real time ultrasound guidance was used to confirm that the needle was anterior to the rectal wall and posterior to the prostate and therefore within Denovillier's space. This process is depicted in FIGS. 1-3, with patient 100 having space 102 between rectum 104 and prostate 106 receiving needle 108 into space 102, with needle 108 being in communication with syringe 110 that contains collagen filler 112. The syringe plunger is depressed to introduce collagen filler 112 into space 102.

Once it was confirmed that the normal saline was within Denovillier's space, the protocol proceeded to the injection of human collagen using the same 5.5 inch gauge 18 spinal needle. Each of the 10 men who entered into the protocol received 20 cc's of human collagen. Their prostate volumes ranged from 35 cc up to 90 cc's.

Following placement of 20 cc's of human collagen, the needle was removed and then the ultrasound transducer. Approximately, 5 days following the collagen injection each man underwent a second CT simulation to obtain a second IMRT radiation computer treatment plan with the collagen injection. Five days were provided to allow reabsorption of the normal saline and the human collagen to "settle" within Denovillier's space.

Figure 4:
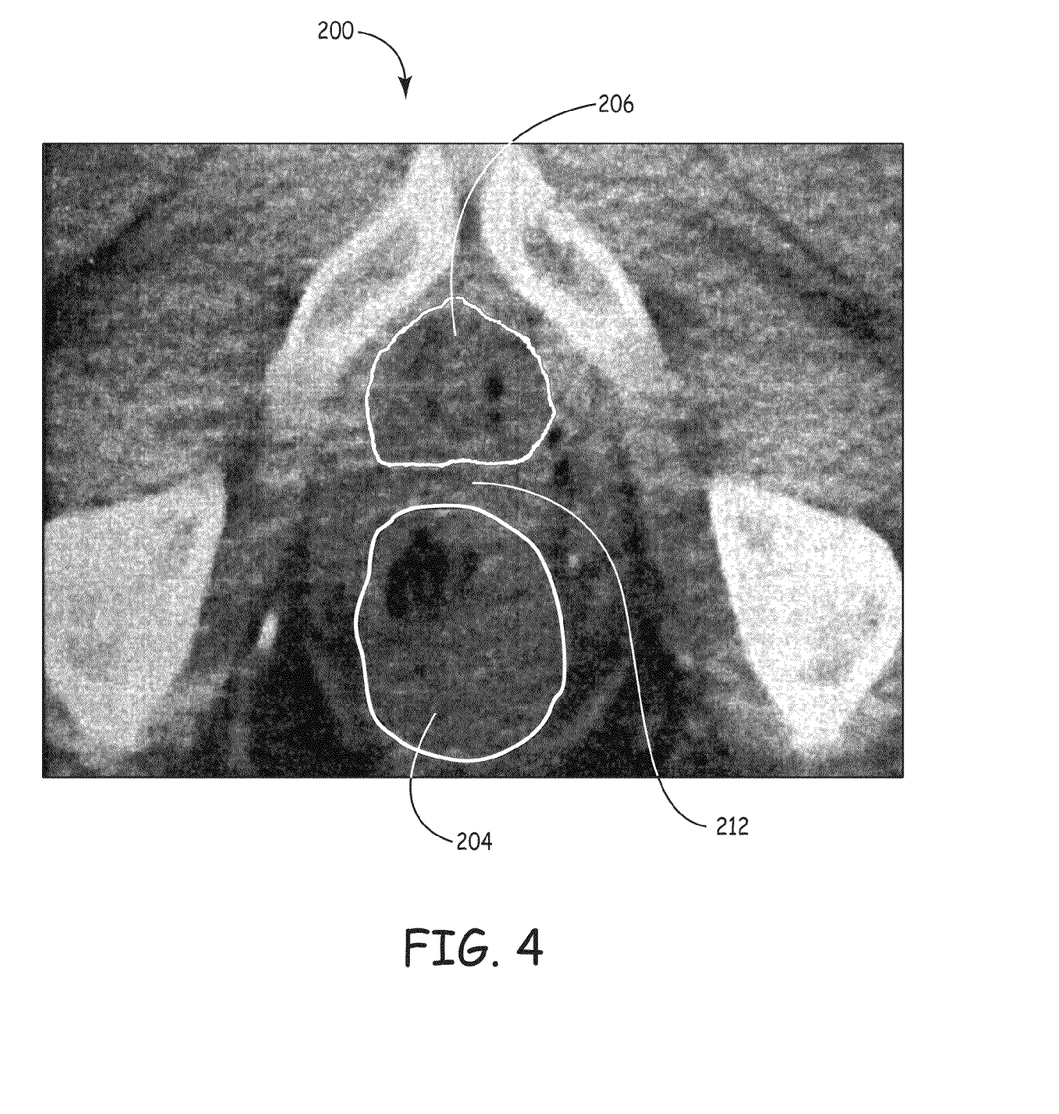
FIG. 4 depicts a computer tomography (CT) image of a patient's pelvis showing a collagen filler placed between the prostate and rectum of the patient.

FIG. 4 depicts a CT scan of a man that received a collagen filler. The man 200 received about 20 cc of collagen filler into the space 212 between rectum 204 and prostate 206. The space 204 is enlarged so that the radiation exposure of rectum 204 is reduced.

The first and second IMRT radiation computer treatment plans were compared to evaluate the displacing properties of human collagen and assess the reduction in radiation dose to the rectum. A third IMRT radiation computer treatment plan was obtained on the last day of treatment to confirm that there had been minimal change throughout their treatment.

During the 2 months of external beam radiation, each person was interviewed on a weekly basis. Quality of life issues were assessed regarding their urinary and bowel habits. CT scans were obtained 6 months and 12 months following completion of their radiotherapy to monitor absorption of human collagen.

Results: Each man who elected to proceed with the ongoing protocol tolerated the collagen injection very well. No one reported symptoms suggestive of an allergic reaction. Three men reported a sensation similar to a light rectal pressure that resolved 3-4 hours after the injection. One man experienced urinary retention and required placement of a Foley catheter. The catheter was removed 3 days after the injection without difficulty or recurrence. It is believed that the urinary retention was secondary to the pudendal nerve block.

All men received prostate treatment to a dose of 75.6 Gy in 42 fractions. Their treatment was delivered using an IMRT 6-field technique. Conventionally, a highly positive outcome is if 30% of the rectum receives 45 Gy or less and 10-15% receives 60 Gy or more.

All of the patients had 20-25% of the rectum receiving 45 Gy or less prior to the collagen injection. Following the collagen injection, 7-15% or the rectum received 45 Gy or less. Moreover, <5% of the rectum received a dose of 60 Gy or more.

All men who received a collagen injection prior to their radiation treatments experienced no change in their bowel habits. Interestingly, one man underwent an unplanned flexible sigmoidoscopy 6 months after completing his radiotherapy. His physician who performed the sigmoidoscopy reported an entirely normal exam without any evidence of radiation treatments.

Five of the 10 men experienced urinary frequency, diminished urinary flow and urgency. Four men elected to be treated with an alpha 1 blocker (Flomax) with success.

The invention has been described in language more or less specific as to structural and methodical features and by reference to detailed examples and methodologies. It is to be understood, however, that the invention is not limited to the specific features shown and described, since the means herein disclosed comprise preferred forms of putting the invention into effect, and the examples are not meant to limit the scope of the invention. It should be understood that variations and modifications may be made while remaining within the spirit and scope of the invention, and the invention is not to be construed as limited to the specific embodiments described or as shown in the drawings. All patents, patent applications, journal references, and publications referenced herein are hereby incorporated by reference herein.

The invention claimed is:

1. A method of delivering a therapeutic dose of radiation to a patient comprising introducing a biocompatible, biodegradable filler between an organ and a nearby tissue to increase a distance between the organ and the tissue, and treating the tissue with the therapeutic dose of radiation so that the presence of the filler causes the organ to receive less of the dose of radiation compared to the amount of the dose of radiation the organ would receive in the absence of the filler, wherein the filler is introduced as an injectable material and is a gel in the patient, and wherein the filler is removable by biodegradation in the patient.

2. The method of claim 1 wherein the organ comprises an ovary.

3. The method of claim 1 wherein the organ is at least part of a nerve.

4. The method of claim 1 wherein the organ comprises a bone.

5. The method of claim 1 wherein the organ is located in a brain.

6. The method of claim 1 wherein the filler comprises a member of the group consisting of polylactide, polyglycolide, polycaprolactone, and poly(alpha-hydroxy acid).

7. The method of claim 1 wherein the filler comprises alginate.

8. The method of claim 1 wherein the filler comprises gelatin.

9. The method of claim 1 wherein the filler comprises fibrin or fibrinogen.

10. The method of claim 1 wherein the filler comprises albumin.

11. The method of claim 1 wherein the filler comprises polyethylene glycol.

12. The method of claim 1 wherein the filler comprises a thixotropic polymer.

13. The method of claim 1 wherein the filler comprises a thermoreversible polymer.

14. The method of claim 1 wherein the filler comprises at least one therapeutic agent.

15. The method of claim 1 wherein the at least one therapeutic agent is a member of the group consisting of an anti-inflammatory drug, an antibiotic, an antimycotic, a hemostat, a steroid, and an analgesic.

16. The method of claim 1 wherein the filler is biodegradable in vivo in between three months and twelve months.

17. The method of claim 1 wherein the biocompatible, biodegradable material consists essentially of collagen.

18. The method of claim 1 wherein the filler comprises at least one polysaccharide.

19. The method of claim 1 wherein the at least one polysaccharide comprises hyaluronic acid.

20. The method of claim 1 wherein the filler material comprises a synthetic polymer.

21. The method of claim 1 wherein the filler further comprises a member of the group consisting of a degradation inhibitor, a radio opaque marker, and an osmotic agent that causes water to become associated with the filler material by osmosis.

22. The method of claim 1 wherein the filler further comprises a pH buffering agent.

23. The method of claim 1 wherein the filler occupies a volume in the range of about 10 to about 200 cubic centimeters in the patient.

24. The method of claim 1 wherein the therapeutic dose of radiation is between 70 to 300 Gy, and wherein that the filler causes organ to receive less than 50% of the dose of radiation compared to the amount of the dose of radiation that the organ would have received in the absence of the filler device.

* * * * *

UNITED STATES PATENT AND TRADEMARK OFFICE
CERTIFICATE OF CORRECTION

Page 1 of 1

PATENT NO.      : 8,257,723 B2
APPLICATION NO. : 12/651502
DATED           : September 4, 2012
INVENTOR(S)     : William R. Noyes It is certified that error appears in the above-identified patent and that said Letters Patent is hereby corrected as shown below:

Column 18, line 21, claim 24, after "causes" insert -- the --.

Signed and Sealed this
Twentieth Day of November, 2012

David J. Kappos
*Director of the United States Patent and Trademark Office*